US011969556B2

(12) United States Patent
Andersson (10) Patent No.: US 11,969,556 B2
(45) Date of Patent: Apr. 30, 2024

(54) THERAPEUTIC SOUND THROUGH BONE CONDUCTION (71) Applicant: Cochlear Limited, Macquarie University (AU)

(72) Inventor: Marcus Andersson, Gothenburg (SE)

(73) Assignee: Cochlear Limited, Macquarie University (AU)

( * ) Notice: Subject to any disclaimer, the term of this patent is extended or adjusted under 35 U.S.C. 154(b) by 583 days.

(21) Appl. No.: 17/273,150

(22) PCT Filed: Dec. 19, 2019

(86) PCT No.: PCT/IB2019/001373
§ 371 (c)(1),
(2) Date: Mar. 3, 2021

(87) PCT Pub. No.: WO2020/128627
PCT Pub. Date: Jun. 25, 2020

(65) Prior Publication Data
US 2021/0322719 A1    Oct. 21, 2021

Related U.S. Application Data (60) Provisional application No. 62/783,496, filed on Dec. 21, 2018.

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2205/3375* (2013.01);
(Continued)

(58) Field of Classification Search
USPC ........................................................ 73/19.03
See application file for complete search history.

(56) References Cited

U.S. PATENT DOCUMENTS 10,111,017 B2 * 10/2018 Hillbratt ............. H04R 25/606
10,412,510 B2 *  9/2019 Bervoets ............ H04R 25/606
(Continued)

FOREIGN PATENT DOCUMENTS

AU    2011202531 A1 * 12/2011  ........... H04R 25/606
CN       1976540 A  *  6/2007  ............... H04R 1/28
(Continued)

OTHER PUBLICATIONS

International Search Report and Written Opinion in counterpart International Application No. PCT/IB2019/001373, dated Jun. 16, 2020, 10 pages.
(Continued)

*Primary Examiner* — Clayton E. LaBalle
*Assistant Examiner* — Warren K Fenwick
(74) *Attorney, Agent, or Firm* — Edell, Shapiro & Finnan, LLC (57) ABSTRACT

Therapeutic sound is provided through a bone conduction apparatus. A patient having a mental disorder is selected and provided with a bone conduction apparatus. A therapeutic signal generator generates a therapeutic signal for ameliorating the mental disorder. A vibratory actuator of the bone conduction apparatus vibrates based on the therapeutic signal, which causes the patient to perceive a therapeutic sound percept.

18 Claims, 5 Drawing Sheets

(52) U.S. Cl.
CPC . *A61M 2205/3592* (2013.01); *A61M 2205/70* (2013.01); *A61M 2210/02* (2013.01)

(56) References Cited

U.S. PATENT DOCUMENTS

| | | | | |
|---|---|---|---|---|
| 11,141,559 | B2* | 10/2021 | Hanbury | A61M 21/02 |
| 11,445,311 | B2* | 9/2022 | Bervoets | H04R 25/606 |
| 11,679,231 | B2* | 6/2023 | Hanbury | A61M 21/02 600/28 |
| 2014/0286513 | A1* | 9/2014 | Hillbratt | G01R 31/2829 381/326 |
| 2015/0110322 | A1* | 4/2015 | Andersson | H04R 25/552 381/326 |
| 2015/0140528 | A1* | 5/2015 | Sikstrom | A61M 21/00 434/236 |
| 2015/0297109 | A1* | 10/2015 | Garten | A61B 5/316 600/28 |
| 2016/0198981 | A1* | 7/2016 | Demir | G01L 1/144 600/587 |
| 2016/0296799 | A1* | 10/2016 | Macagnano | A61B 5/6814 |
| 2017/0171677 | A1* | 6/2017 | Norris | A61N 7/00 |
| 2018/0014130 | A1* | 1/2018 | Lunner | A61F 11/06 |
| 2018/0242088 | A1* | 8/2018 | Hillbratt | A61B 5/4851 |
| 2020/0121544 | A1* | 4/2020 | George | A61H 9/00 |
| 2021/0138232 | A1* | 5/2021 | Paz | A61N 1/36021 |

FOREIGN PATENT DOCUMENTS

| | | | |
|---|---|---|---|
| KR | 10-2015-0134561 A | 12/2015 | |
| KR | 10-1665284 B1 | 10/2016 | |
| KR | 101665284 B1 * | 10/2016 | H04R 1/10 |

OTHER PUBLICATIONS

Baijot, Simon et al., "Neuropsychological and neurophysiological bene"ts from white noise in children with and without Adhd", DOI 10.1186/s12993-016-0095-y, Mar. 15, 2016, 13 pages.

Söderlund, Goran et al., "Listen to the noise: noise is beneficial for cognitive performance in ADHD", doi:10.1111/i.1469-7610.2007.01749.x, Jan. 24, 2007, 8 pages.

Taylor, Paul, "White noise may be as effective as drugs for ADHD", Sep. 30, 2010, 2 pages.

* cited by examiner

THERAPEUTIC SOUND THROUGH BONE CONDUCTION

This application is being filed on Dec. 20, 2019, as a PCT International Patent application and claims priority to U.S. Provisional patent application Ser. No. 62/783,496, filed Dec. 21, 2018, the entire disclosure of which is incorporated by reference in its entirety.

BACKGROUND

People sometimes listen to audio or other sounds while preforming a task to provide entertainment or to improve concentration. And studies have explored the possibility of using white noise to improve the cognitive function of people with attention deficit hyperactivity disorder. Traditionally, such sounds are provided through speakers or headphones. However there are circumstances where the use of headphones and speakers can be inappropriate, such as in certain classrooms. The use of headphones and speakers can also have other drawbacks.

SUMMARY

Technology disclosed herein includes systems, apparatuses, devices, and methods that provide therapeutic sound through bone conduction.

In an example, there is a method including: selecting a patient having a mental disorder; providing a bone conduction apparatus to the patient; generating a therapeutic signal for ameliorating the mental disorder; and vibrating, using the therapeutic signal, a vibratory actuator of the bone conduction apparatus to cause the patient to perceive a therapeutic sound percept.

In some examples, the method further includes: tracking a head movement of the patient to generate head movement data; and modifying the generating of the therapeutic signal based on the head movement data. In some examples, generating the therapeutic signal includes compensating the therapeutic signal for soft tissue attenuation. In some examples, modifying the generating of the therapeutic signal includes: modifying an intensity level of the therapeutic signal; or modifying a type of therapeutic signal. In some examples, the method further includes: measuring an ambient noise level to generate ambient noise level data; and modifying the generating of the therapeutic signal based on the ambient noise level data. In some examples, the method further includes monitoring usage of the bone conduction apparatus to generate usage data. In some examples, generating the therapeutic signal includes: generating white noise, pink noise, or brown noise. In some examples, generating the therapeutic signal includes: playing a stored therapeutic sound loop. In some examples, the method further includes: wirelessly receiving the therapeutic signal at the bone conduction apparatus. In some examples, selecting a patient having a mental disorder includes selecting a patient being treated for a mental disorder with a treatment plan including the use of a pharmaceutical. In some examples, causing the patient to receive the therapeutic sound percept supplements the treatment plan.

In another example, there is a bone conduction apparatus. The bone conduction apparatus includes: a housing; a therapeutic sound system configured to solely generate therapeutic sound configured to address an mental disorder, the therapeutic sound system comprising: a signal generator configured to generate a therapeutic signal; and a vibratory actuator disposed in the housing and configured to vibrate in response to the therapeutic signal; and a coupling apparatus to facilitate transfer of vibrations from the vibratory actuator to a cochlea of a recipient of the bone conduction apparatus via the recipient's skull.

In some examples, bone conduction apparatus further includes: a memory having stored thereon one or more therapeutic sound loops, and the signal generator is configured to generate the therapeutic signal from the one or more therapeutic sound loops. In some examples, the bone conduction apparatus further includes: a gyroscopic sensor configured to obtain head movement data when the bone conduction apparatus is worn by the recipient; or an accelerometer configured to obtain head acceleration data when the bone conduction apparatus is worn by the recipient. In some examples, the signal generator is remote from the housing. In some examples, the signal generator is configured to, when generating the therapeutic signal, compensate for soft tissue attenuation during transmission of the vibrations to the cochlea of the recipient of the bone conduction apparatus.

In a further example, there is a method including: providing a bone conduction apparatus to a recipient prior to the recipient performing a task; and while the recipient is performing the task and wearing the bone conduction apparatus: generating a predetermined therapeutic signal; and vibrating, based on the predetermined therapeutic signal, a vibratory actuator of the bone conduction apparatus to cause the recipient to receive a therapeutic sound percept.

In examples, the method further includes: monitoring a usage of the bone conduction apparatus to generate usage data; tracking head movement of the recipient to generate head movement data; and providing the usage data and the head movement data as output. In examples, the method further includes calibrating the bone conduction apparatus to the recipient to generate calibration data, and the generating the predetermined therapeutic signal includes generating the predetermined therapeutic signal based on the calibration data. In examples, the method further includes receiving a profile identifier; and selecting calibration data from a calibration data set using the profile identifier. In examples, generating the predetermined therapeutic signal includes generating the predetermined therapeutic signal based on the selected calibration data. In examples, generating the predetermined therapeutic signal includes: generating a white noise signal; generating a pink noise signal; or generating a brown noise signal.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Audio signals can be therapeutic. Traditional techniques for providing audio include the use of speakers or headphones. However such devices can negatively affect the ability of a person to perform certain tasks and can negatively affect nearby individuals. For example, headphones can occlude a wearer's ear, which can limit the ability of the wearer to hear other sounds (e.g., lectures) that rely on an open ear. As another example, while speakers do not block a person's ears, speakers can be disruptive to others and lack discretion. Examples disclosed herein can address these and other challenges through the use of a bone conduction apparatus to cause a recipient to perceive a therapeutic sound percept.

In contrast to conventional audio-producing devices (e.g., speakers and headphones), which rely primarily on the principles of air conduction, bone conduction devices produce vibrations that are transferred through the skull. The transferred vibrations reach the cochlea and cause motion of the perilymph and stimulation of the auditory nerve, which results in the perception of the received sound, such as a therapeutic sound percept.

Therapeutic sound percepts are sound percepts that have, are thought to have, or are selected to have a therapeutic effect, such as ameliorating a disorder (e.g., lessening one or more symptoms of the disorder). In examples, the use of the bone conduction apparatus to cause a therapeutic sound percept is part of a treatment regimen for addressing a disorder. For example, the use of the bone conduction apparatus can be used in addition to or instead of a traditional treatment regimen for the disorder (e.g., the use of pharmaceuticals). Disclosed examples include the use of vibrations generated by a bone conduction apparatus to cause a therapeutic sound percept in a patient having (e.g., diagnosed as having or thought to have) a mental disorder, such as an attention disorder (e.g., ADHD), Tourette's syndrome, drug abuse, or Obsessive Compulsive Disorder (OCD). In some examples, using bone-conducted vibrations to induce a therapeutic sound percept can treat disorders other than mental disorders, such as tinnitus. Example sources usable to generate therapeutic sound percepts include noise signals.

Noise signals (or simply "noise") as used herein are signals usable to cause hearing percepts in a recipient (e.g., by causing a vibratory actuator 118 to vibrate) that are not designed to convey specific information perceptible by the recipient. For example, such signals can be contrasted with music (e.g., which conveys musical structure through the arrangement of particular notes), conversational speech (e.g., which conveys information provided by a speaker), and microphone output of a hearing device (e.g., which is designed to convey contemporaneous information of the environment surrounding the wearer of the hearing device), which are designed to convey specific meaning. In examples, noise includes signals produced by a stochastic process, such as white noise, brown noise, or pink noise. In examples, various colors of noise can be produced, such as white noise (e.g., noise having substantially equal power per hertz over a frequency band), pink noise (e.g., noise having substantially equal power per octave over a frequency band), blue noise (e.g., noise having a spectral density proportional to the frequency over a frequency band), or brown noise (e.g., noise having a spectral density inversely proportional to the square of the frequency), among other colors or types of noise. Noise can also include signals that are generated based on natural background sources, such as the sound of rain, a thunderstorm, waves, forest sounds, birdsong, wind, fire, or combinations thereof. Noise can also include signals that are generated based on other sources such as background sounds from traffic, coffee shops, airplanes, or trains. While such background noise can be recognized as coming from a specific source or as containing information (e.g., that a bird is singing or spoken phrases emerging from the buzz of a coffee shop), they are not designed to convey specific information perceptible by the recipient.

The perception of noise, or therapeutic signals in general, provided through bone conduction can be different from how that same therapeutic signal in general would be perceived if transmitted through conventional air-conduction audio devices, such as speakers or headphones. For instance, if white noise was a desired treatment and it were transmitted through a transcutaneous bone conduction system, high frequencies can be lost due to attenuation from the recipient's tissue (e.g., skin). Differences in tissue thickness and individual anatomy can create variation in attenuation among individuals. As a result, the attenuation can turn a desired therapeutic white noise into pink noise or even brown noise depending on the amount of attenuation. In some examples herein, the output of the bone conduction apparatus 100 to cause a therapeutic hearing percept is generated in a way that compensates for attenuations. The compensation can include a general, non-individualized modification of the generation of therapeutic signals or customized modification for specific recipients (e.g., based on a fitting session).

Additional examples disclosed herein can modify the generation of therapeutic sound based on sensor data, such as data obtained from an accelerometer, gyroscopic sensor, a microphone, or an EEG (electroencephalogram) among other sensors. In an example, one or more sensors are used to obtain head movement data of the recipient, and the data is used to modify the intensity or type of vibrations produced by the bone conduction apparatus. For instance, an increase in head movement can indicate an increase in distraction in a recipient having an attention disorder (e.g., ADHD), so the intensity of vibrations is increased to ameliorate the increased distraction. In another example, the noise of the environment around the bone conduction apparatus is detected via the microphone, and the vibrations are modified in response thereto. The sensor data can further be used to monitor compliance with a treatment plan as well as to determine whether a treatment plan is having an intended affect.

In examples, the generation of the vibrations based on a therapeutic signal is based on a treatment schedule. For instance, a treatment schedule can specify a type of therapeutic signal and an amount of time for which the vibrations are to be provided. In examples, during treatment there may be a period of time in which the vibrations are provided followed by a period in which the vibrations are not provided followed again by a period of time in which the vibrations are provided. In examples, the treatment schedule specifies that an intensity level of the vibrations is increased or decreased over time.

In examples herein, the therapeutic sound is produced by a dedicated device with the primary purpose of producing vibrations based on a therapeutic signal rather than acting as a bone conduction auditory prosthesis. For instance, individuals suffering from conductive hearing loss may receive an auditory prosthesis that generates mechanical motion of the cochlea fluid to cause a hearing percept indicative of the sonic environment around the recipient. As a particular example, such an auditory prosthesis receives acoustic sound signals from a microphone and converts the sound signals into electrical signals for use in actuating a vibrator to cause a hearing percept. By contrast, rather than producing a hearing percept indicative of a current sonic environment around the recipient, disclosed examples can produce a predetermined therapeutic sound percept. As a particular example, a bone conduction device disclosed herein can be predetermined (e.g., preconfigured) to produce a white noise signal when activated. Beneficially, a dedicated therapeutic-signal-generating device can be constructed more simply than an auditory prosthesis. The dedicated device can advantageously have a lower cost, an improved battery life, decreased weight, reduced size, and other beneficial characteristics compared to more complex devices. For instance, rather than using a high-resolution actuator capable of generating high-quality vibrations representative of ambient sound around the device (e.g., as with bone conduction auditory prostheses), certain devices disclosed herein can be relatively lower-resolution. The vibratory actuator of such devices can be tuned to produce vibrations based on predetermined therapeutic signals (e.g., white noise) rather than arbitrary input (e.g., from a microphone or sound source, such as a media player). In examples, the devices disclosed herein can lack a microphone, lack feedback-reducing circuitry, or other components.

In other examples, the therapeutic signal components disclosed herein can be added as one or more modules to auditory prostheses to expand the capabilities of such devices. For instance, the auditory prosthesis can be a cochlear implant, a bone conduction device (e.g., percutaneous bone conduction devices, transcutaneous bone conduction devices, active bone conduction devices, and passive bone conduction devices), or a middle ear stimulators, among others.

System

Figure 1:
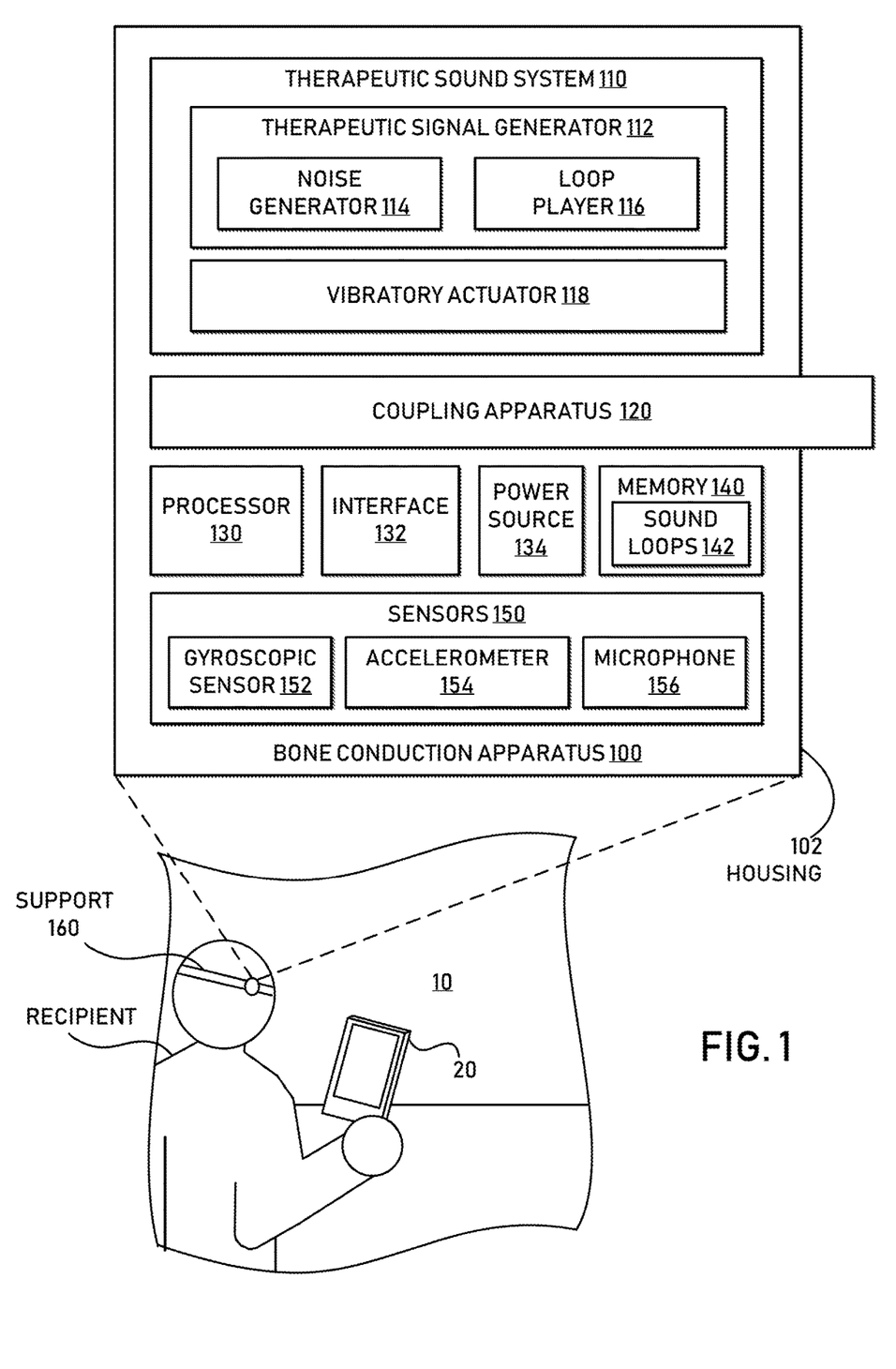
FIG. 1 illustrates an example bone conduction system for providing therapeutic sound.

FIG. 1 illustrates an example bone conduction system 10 for providing therapeutic sound. The bone conduction system 10 includes one or more bone conduction apparatuses 100 and, in some examples, a recipient computing device 20.

The bone conduction apparatus 100 is an apparatus that generates vibrations in response to a therapeutic signal to cause a recipient (e.g., a wearer of the bone conduction apparatus 100) to perceive a therapeutic sound percept. In the illustrated example, the bone conduction apparatus 100 includes a housing 102 within which are a therapeutic sound system 110, a coupling apparatus 120, a processor 130, an interface 132, a power source 134, a memory 140, and one or more sensors 150. The bone conduction apparatus 100 can further include a support 160 by which the bone conduction apparatus 100 is worn by the recipient.

The housing 102 is a casing that encloses one or more components of the bone conduction apparatus 100. The housing 102 can provide environmental resistance, such that it prevents or resists water or dust from affecting one or more of the components. In many examples, includes components to facilitate the wearing of the bone conduction apparatus 100 by the recipient. In example, the bone conduction apparatus 100 includes a fastener (e.g., a snap-in coupler) to couple the housing 102 or another component, such as the coupling apparatus 120, to the support 160.

The therapeutic sound system 110 is a system of the bone conduction apparatus 100 that generates vibrations to cause a therapeutic sound percept to be perceived by the recipient when the bone conduction apparatus 100 is worn by the recipient. The therapeutic sound system 110 includes a therapeutic signal generator 112 and a vibratory actuator 118.

The therapeutic signal generator 112 is one or more components of the therapeutic sound system 110 that produces a signal for causing the vibratory actuator 118 to vibrate in a manner that causes a therapeutic sound percept. Examples of such components include a noise generator 114 and a loop player 116. The noise generator 114 is a software or hardware component that generates a noise signal. The loop player 116 is a software or hardware component that plays loops of content.

The vibratory actuator 118 is a component that converts electrical signals into vibrations. For example, the vibratory actuator 118 is electrically connected to the therapeutic signal generator 112, receives electrical signals therefrom, and produces vibrations based thereon. In examples, vibratory actuator 118 includes a piezoelectric transducer or an electro-magnetic transducer. The vibratory actuator 118 is mechanically coupled to the coupling apparatus 120 for transferring vibrations to the recipient.

In some examples, the vibratory actuator 118 is a low-resolution vibratory actuator 118. For instance, where the bone conduction apparatus 100 is configured as a dedicated therapeutic-sound-percept-causing device (e.g., rather than being a more general-purpose device for reproducing music or an ambient sound environment), the vibratory actuator 118 can be made to be low resolution or tuned to the kinds of vibrations that would be produced based on the therapeutic signal. In examples, the vibratory actuator 118 is an unbalanced actuator rather than a balanced one. In examples, the vibratory actuator 118 is tuned, selected, or otherwise configured to resist attenuation of transmitted signals by the recipient's tissue. For instance, a vibrating mass of the vibratory actuator can be tuned (e.g., by having a decreased or otherwise modified weight) to produce output having boosted high frequencies, such that when the vibrations are attenuated, a desired therapeutic sound percept is perceived by the recipient.

The coupling apparatus 120 is a component of the bone conduction apparatus 100 that facilitates the transfer of vibrations from the vibratory actuator 118 to the recipient. In many examples, the coupling apparatus 120 is at least partially disposed outside of the housing 102. For instance, the coupling apparatus 120 can include a plate adapted to contact skin of a recipient for transferring vibrations to the recipient through the skin. The plate can be connected to the vibratory actuator 118 via a shaft that extends through an opening in the housing 102. In some examples, a plate or other portion for conducting vibrations through the skin of the recipient is provided by the support 160 rather than the coupling apparatus 120 directly. In such examples, the coupling apparatus 120 can have a fastener (e.g., a snap-fit coupler) for mechanically coupling the coupling apparatus to the conduction portion of the support 160.

The processor 130 is one or more processing units, such as one or more central processing units (CPUs). In examples, the processor 130 executes instructions to produce results and control one or more aspects or operations of the bone conduction apparatus 100 described herein.

The interface 132 is one or more components that facilitate interaction between the bone conduction apparatus 100 and another device (e.g., a computing device, such as the recipient computing device 20) or the recipient. The interface 132 can include one or more input components such as buttons (e.g., for powering on or off the device or changing one or more settings). The interface 132 can also include one or more output components such as a light (e.g., for use in indicating power), a display, or a speaker. The interface 132 can include one or more communication components, such as one or more radio antennas (e.g., for WI-FI, BLUETOOTH, or cellular connections), data ports (e.g., a USB port), or power ports.

The power source 134 is a component that provides operational power to one or more other components of the bone conduction apparatus 100. In many examples, the power source 134 includes one or more rechargeable or disposable batteries. The power source 134 can also include a charging circuit for charging a rechargeable battery. In some examples, the charging circuit can include an induction coil configured to permit wireless recharging of the power source 134 when located in proximity to a charging station. In some examples, the power source 134 includes an energy harvesting component that converts mechanical actuation (e.g., via an internal pendulum or slidable electrical inductance charger actuated through movement of the recipient) to charge the power source 134.

The memory 140 is a computer-readable storage medium. The memory 140 can be volatile (such as RAM (Random-Access Memory)), non-volatile (such as ROM (Read-Only Memory), flash memory, etc.), or some combination thereof. The memory 140 can be transitory or non-transitory. In examples, the memory 140 stores instructions to implement modules (e.g., the noise generator 114 or loop player 116) or perform methods disclosed herein. In the illustrated example, the memory 140 stores one or more sound loops 142.

Each sound loop 142 of the one or more sound loops 142 is data representative of a loop of sound playable by the loop player 116 to produce a therapeutic signal. For example, the bone conduction apparatus can store a five second audio sample of audio that loops substantially seamlessly (e.g., as an audio file, such as in an MP3 or WAV format). For instance, the audio can be a pre-generated loop of noise (e.g., white noise, brown noise, or pink noise). In examples, the sound loops 142 are loaded on the bone conduction apparatus 100 during manufacturing. In other examples, the sound loops 142 are loadable from the recipient computing device 20. For instance, an application on the user computing device can modify the memory 140 to add, modify, or delete one or more of the sound loops 142.

The one or more sensors 150 are components of the bone conduction apparatus 100 that take a measurement and produce data as output. In the illustrated example, the one or more sensors 150 can include a gyroscopic sensor 152, an accelerometer 154, and a microphone 156.

The gyroscopic sensor 152 is a sensor that measures orientation and angle data of the bone conduction apparatus 100 and produces output as a result. The accelerometer 154 is a component of the bone conduction apparatus 100 that measures acceleration of the device and produces acceleration data as output. The microphone 156 is a component that converts sound into data. In some examples, the sensors 150 include an EEG (electroencephalogram) sensor to obtain data regarding the recipient's brain activity. The brain activity can be used to directly or indirectly to monitor symptoms or indications of a disorder of the recipient.

The support 160 is a component for attaching the bone conduction apparatus 100 to the recipient's head. For examples, the support 160 can hold the coupling apparatus 120 of the bone conduction apparatus 100 against the recipient's head in a manner and location conducive to transmit vibrations from the vibratory actuator 118 to the recipient to cause a hearing percept. In an example, the support 160 holds the coupling apparatus 120 against a location behind an ear canal of the recipient's ear. In an example, the location is proximate a temporal bone of the recipient. In some examples, the support 160 is an elastic headband, ear hook, or hat wearable by the recipient. In other examples, the support 160 places the bone conduction apparatus 100 in connection with oral anatomy (e.g., an upper tooth). The support 160 can be an adhesive patch for adhering the bone conduction apparatus 100 to a specific location on the recipient. In further examples, the support 160 has one or more characteristics of the bone conduction support described in US 2013/0089229, titled "Bone Conduction Device Support", which is hereby incorporated by reference in its entirety for any and all purposes. In still other examples, the support 160 has one or more characteristics of the wearable band described in US 2018/0288537, titled "Wearable Band for Facilitating Hearing", which is hereby incorporated by reference in its entirety for any and all purposes.

While the bone conduction apparatus 100 is shown as having a plurality of components within the housing 102, described components need not all be disposed in the housing 102. The bone conduction apparatus 100 can include components in separate housings that cooperate to provide one or more features described herein. In examples, the bone conduction apparatus 100 cooperates with the recipient computing device 20 to provide functionality.

In certain situations, it can be desirable to provide vibrations to both the left cochlea and the right cochlea of a recipient. The bone conduction apparatus 100 can accommodate this in a variety of ways. In some examples, a recipient wears two bone conduction apparatuses 100: a left bone conduction apparatus 100 and a right bone conduction apparatus 100. The multiple bone conduction apparatuses 100 can operate independently or cooperatively (e.g., by communicating with each other to, for example, providing a same therapeutic sound at substantially the same time). In other examples, the recipient wears a single bone conduction apparatus 100 that includes a left vibratory actuator 118 and a right vibratory actuator 118 that provide vibrations to the recipient via respective left and right coupling apparatuses 120. The left and right vibratory actuators 118 can actuate based on signals from a same therapeutic signal generator 112. In still other examples, there is a single vibratory actuator 118 configured to provide suitable vibrations to both ears of a recipient. In examples, the single vibratory actuator 118 is provided on a single side (e.g., left or right) of the recipient's skull and the skull sufficiently conducts the vibrations to the other side to produce a hearing percept of a sufficiently therapeutic quality. In examples, the output vibrations are piped to left and right sides of the recipient's skull by the coupling apparatus 120. In yet other examples, there is a single bone conduction apparatus 100 that is disposed at a location on the recipient's skull or neck that transmits vibrations to the recipient's skull such that the hearing percept occurs at both the left cochlea and the right cochlea. In examples, the bone conduction apparatus 100 can be implemented as an under-lip bone conduction device, for example, as described in US 2016/0234611, titled "Under-Lip Bone Conduction Device", incorporated herein by reference for any and all purposes.

The recipient computing device 20 is a computing device associated with the recipient of the bone conduction apparatus 100. In many examples, the recipient computing device 20 is a cell phone, tablet computer, or laptop computer, but the recipient computing device 20 can take other forms.

In some examples, one or more settings of the bone conduction apparatus 100 are modifiable by an application operating on the recipient computing device 20. For instance, the recipient computing device 20 can be connected to the bone conduction apparatus 100 via a wireless connection through the interface 132. The recipient computing device 20 provides a user interface (e.g., a touch screen user interface) via which input from the recipient is received. Based on the input (e.g., a selection of a setting to change), the application operating on the recipient computing device 20 sends a message to the interface 132, which causes a change to the operation of the bone conduction apparatus 100 based thereon (e.g., by modifying a parameter used to control the operation of the bone conduction apparatus 100).

In examples, the recipient computing device 20 includes a therapeutic sound system application that operates on the recipient computing device 20 and cooperates with the bone conduction apparatus 100. For instance, the therapeutic sound system application can control one or more aspects of the bone conduction apparatus 100 (e.g., based on input received from the recipient), obtain data from the bone conduction apparatus 100, or transmit data to the bone conduction apparatus 100. The recipient computing device 20 can connect to the bone conduction apparatus 100 using, for example, a wireless radiofrequency communication protocol (e.g., BLUETOOTH). The therapeutic sound system application can transmit or receive data from the bone conduction apparatus 100 over such a connection. In some examples, the application can stream therapeutic audio or a therapeutic signal to the bone conduction apparatus 100. For example, the therapeutic signal generator 112 can be located in the recipient computing device and can transmit a therapeutic signal to the bone conduction apparatus 100 for use in actuating the vibratory actuator 118.

Method for Causing a Recipient to Perceive a Therapeutic Sound Percept Using a Bone Conduction Apparatus.

Figure 2:
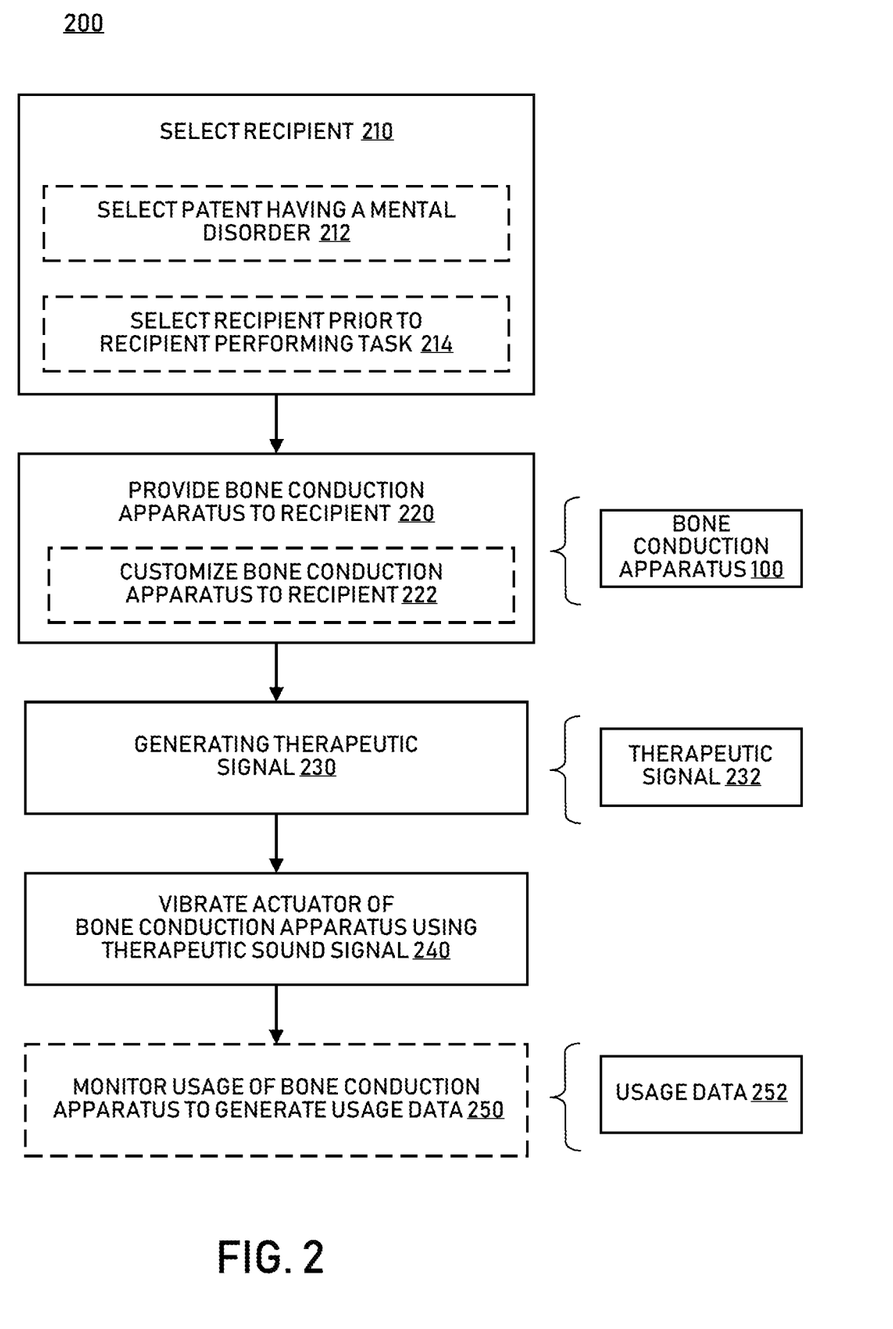
FIG. 2 illustrates a method for providing therapeutic sound.

FIG. 2 illustrates an example method 200 for causing a recipient to perceive a therapeutic sound percept using the bone conduction apparatus 100. While the method is described in relation to the bone conduction apparatus 100, other apparatuses can be used. In the illustrated example, the method 200 begins with operation 210.

Operation 210 includes selecting a recipient. Selecting the recipient can include determining that an individual can benefit from therapeutic sounds. The determination that the individual can benefit from the therapeutic sounds can be based on a variety of factors, such as the individual's health (e.g., based on medical diagnoses about the individual) and the individual's goals (e.g., ameliorating one or more symptoms of a disorder without pharmaceutical intervention or improving performance in a particular area). In some examples, determining that the individual can benefit from therapeutic sounds is based on a trial period. During the trial period, the individual is provided therapeutic sound (e.g., via the bone conduction apparatus 100 or another source such as a speaker or headphones) and monitored (e.g. using one or more sensors 150 to objectively measure treatment efficacy) to determine whether the individual benefitted from treatment using therapeutic sound.

In some examples, operation 210 includes operation 212, which includes selecting a patient having (e.g., diagnosed as having or thought to have) a mental disorder. The mental disorder can include an attention disorder (e.g., ADHD), Tourette's syndrome, narcolepsy, an addiction disorder (e.g., drug abuse), or Obsessive Compulsive Disorder (OCD), among others.

In examples, the use of the bone conduction apparatus 100 to cause a therapeutic sound percept is part of a treatment regimen for addressing a disorder. For example, the bone conduction apparatus 100 can be used in addition to or instead of a traditional treatment regimen for the disorder, such as the use of pharmaceuticals. As a particular example, a treatment regimen can be provided for treating ADHD that includes providing an amount of stimulant medication to a recipient in conjunction with providing an amount of stimulus (e.g. vibrations) provided by the bone conduction apparatus 100.

In some examples, operation 210 includes operation 214, which includes selecting a recipient prior to the recipient performing a task. Providing a therapeutic sound percept can benefit recipients even if the recipient does not have a diagnosed disorder. In some examples, therapeutic sound percepts can be used to improve a recipient's performance (e.g., ability to concentrate) during a task. As such, selecting the recipient can include selecting the recipient prior to performing a task. The task can be a focus-intensive, cognitively-demanding, or stressful task. For instance, the task can be an academic task (e.g., listening to a lecture, taking a test, or completing homework), a business task (e.g., preparing a report), an athletic task (e.g., participating in a race or competition), or a competitive task (e.g., participating in a chess match), among others.

Following operation 210, the flow of the method 200 can move to operation 220.

Operation 220 includes providing a bone conduction apparatus 100 to the recipient, such as the bone conduction apparatus 100. Providing the bone conduction apparatus 100 can include making the bone conduction apparatus 100 available for use, such as by the recipient (e.g., by turning on the bone conduction apparatus 100 or wearing the bone conduction apparatus 100) or by a provider (e.g., a healthcare professional). In examples, providing the bone conduction apparatus 100 include providing the bone conduction apparatus 100 as part of a treatment plan. The treatment plan can include a description of situations in which the recipient should use the bone conduction apparatus 100 to generate a therapeutic sound percept, an amount of time for which the recipient should use the bone conduction apparatus, and particular parameters with which the bone conduction apparatus 100 should be operated. In some examples, the treatment plan is prescribed by the healthcare professional. In examples, aspects of the treatment plan are selected for ameliorating symptoms of a mental disorder.

In examples, operation 220 includes operation 222, which includes customizing the bone conduction apparatus 100 to the recipient. Customizing the bone conduction apparatus 100 can include fitting the bone conduction device to the recipient (e.g. establishing threshold and comfort levels for delivery of therapeutic sound). Customizing the bone conduction apparatus 100 can include setting one or more parameters that affect the generation of a therapeutic signal by the therapeutic signal generator 112. The parameters can affect, for example, an intensity of a therapeutic signal (e.g., a volume of a sound percept caused based on the therapeutic signal), a frequency profile of the therapeutic signal, a type of therapeutic signal (e.g., white noise, brown noise, pink noise, or natural background source), and a source of the therapeutic signal (e.g., whether from the noise generator 114, the loop player 116, or a mix of both), among other aspects. In some examples, the customizing can include or be based on impedance-related phenomena as described in US 2014/0286513, titled "Determining Impedance-Related Phenomena in Vibrating Actuator and Identifying Device System Characteristics Based Thereon", which is hereby incorporated by reference in its entirety for any and all purposes.

Customizing the bone conduction apparatus 100 to the recipient can include setting parameters to compensate for an amount of attenuation caused by the recipient's anatomy. The parameters that compensate for the attenuation can vary depending the kind and amount of attenuation. In some examples, the parameters include parameters that boost or cut an intensity of one or more particular frequency ranges in an output of the therapeutic signal generator 112.

As part of the providing 220, the amount of attenuation caused by the recipient's anatomy can be determined. For instance, a vibratory input can be provided to the recipient using the bone conduction apparatus 100 and a sensor placed on the recipient (e.g., on a tooth of the recipient) measures the vibratory input. A difference between the provided vibratory input and the measured vibratory input is used to determine the amount of attenuation. Based thereon, parameters can be chosen to compensate for the attenuation. In another example, a thickness and quality of the recipient's tissue through which the vibrations will pass is measured. An amount of attenuation can be inferred based on the measurement. In yet another example, the attenuation is measured based on qualitative or quantitative feedback from the recipient. For example, a sound is played for the recipient using a speaker and the same sound is played for the recipient using the bone conduction apparatus 100. The settings of the bone conduction apparatus 100 are then modified until a hearing percept caused by the sound played by the speaker and a hearing percept caused by the sound played by the bone conduction apparatus 100 are substantially the same.

In examples, the customizing is based on a pure tone test. For instance, the bone conduction apparatus 100 produces vibrations that start below hearing threshold for several frequencies and the vibrations are changed above the hearing threshold (or vice versa). Then the signals that resulted in a hearing percept at the edge of the hearing range are used to produce calibration data that compensates for the specific way in which the recipient hears (e.g., based on tissue attenuation or other factors).

Customizing the bone conduction apparatus 100 can include determining one or more kinds of therapeutic signals to be provided and configuring the bone conduction apparatus 100 to provide those therapeutic signals. This can include selecting (e.g., selecting from a library of sound loops or generating a new sound loop 142 customized to the recipient) and adding one or more sound loops 142 to the memory 140 of the bone conduction apparatus 100.

In other examples, customizing the bone conduction apparatus 100 to the recipient includes determining one or more noise generation parameters and applying them to the bone conduction apparatus, such that the noise generator 114 generates the noise according to those parameters. The parameters can include, for example, whether to generate white, pink, or brown noise. The parameters can also include filters that shape the output of the noise generator 114 to have certain characteristics, such as frequency profiles.

Figure 3:
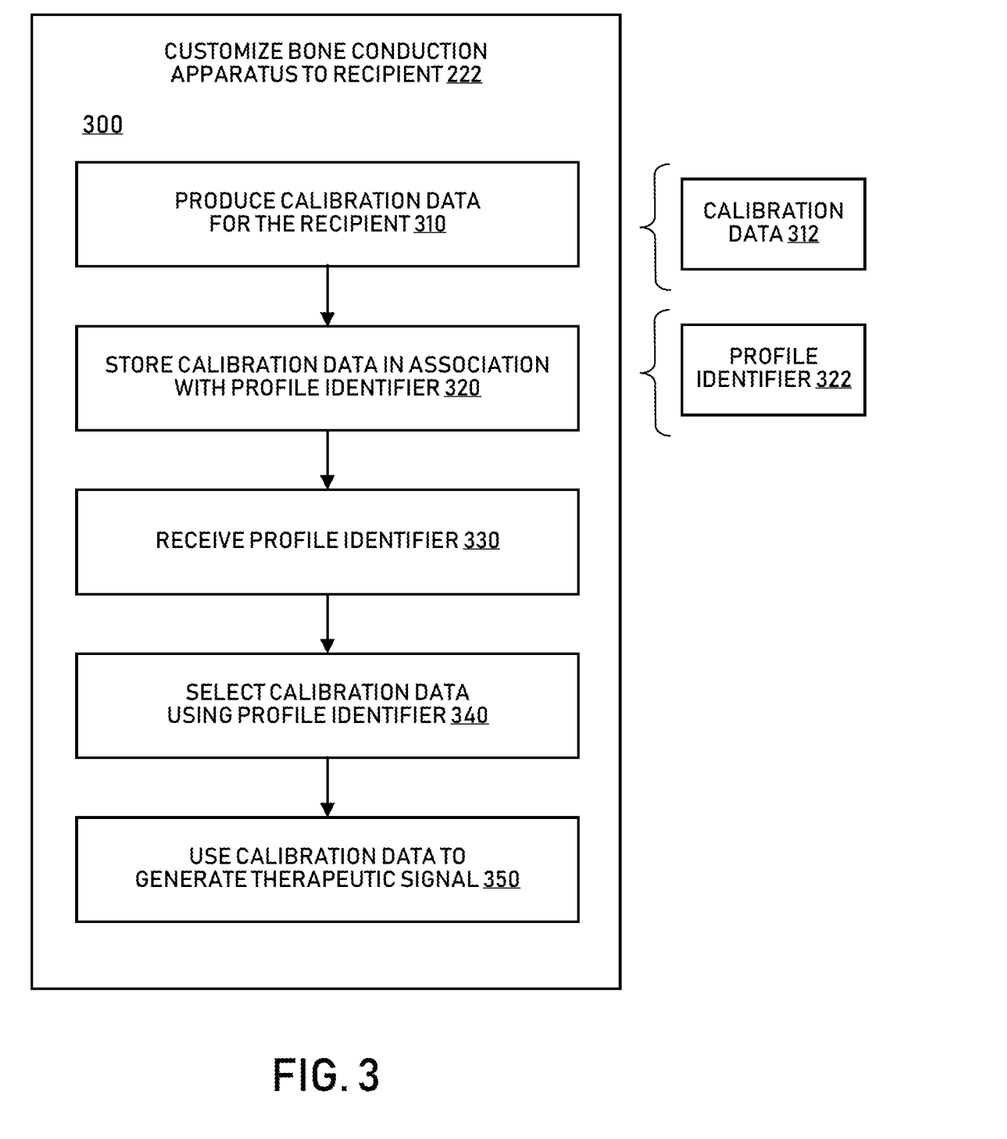
FIG. 3 illustrates a method for customizing the bone conduction apparatus for the recipient.

Additional details regarding operation 222 are described in relation to FIG. 3. Following operation 220, the flow of the method 200 can move to operation 230.

Operation 230 includes generating a therapeutic signal 232. Generating the therapeutic signal 232 can include activating the therapeutic signal generator 112. The therapeutic signal generator 112, once active, can produce the therapeutic signal 232 as output. In examples, the therapeutic signal generator 112 operates to produce the therapeutic signal 232 as output based on one or more parameters. Activating the therapeutic signal generator 112 can include activating the noise generator 114 thereof. A noise signal produced by the noise generator 114 can be the therapeutic signal 232. Activating the therapeutic signal generator 112 can include activating the loop player 116 thereof. For instance, generating the therapeutic signal 232 includes generating the therapeutic signal 232 to ameliorate the mental disorder. Additional details regarding generating the therapeutic signal 232 are described in relation to FIG. 4. Following operation 230, the flow of the method 200 can move to operation 240.

Operation 240 includes vibrating an actuator of the bone conduction apparatus 100 using the therapeutic signal 232. For example, the operation 240 includes providing the therapeutic signal 232 of the therapeutic signal generator 112 to the vibratory actuator 118 to cause the vibratory actuator 118 to vibrate based on the therapeutic signal 232. In some examples, the therapeutic signal 232 is processed by driver circuitry of the vibratory actuator 118, which receives the therapeutic signal 232 and controls the movement of a counter-mass based thereon. In some examples, following operation 240, the flow of the method 200 moves to operation 250.

Operation 250 includes monitoring the usage of the bone conduction apparatus 100 to generate usage data 252. Usage of the bone conduction apparatus 100 can be monitored for a variety of purposes. In some examples, the usage data 252 includes data describing when the bone conduction apparatus 100 generates a vibratory output and for how long. Such usage data 252 can be used to track compliance with a treatment plan for the recipient. The usage data 252 can track the level of noise provided to reduce the risk of noise-induced hearing loss. The usage data 252 can include data regarding the actual or perceived effectiveness of the treatment. For instance, the usage data 252 can include responses to questions regarding the user's perception of the effectiveness of the treatment (e.g., the recipient computing device can query the recipient regarding perceived effectiveness of the treatment and store answers to the queries as usage data 252). In other examples, the usage data 252 can include objective data regarding the recipient (e.g., head movement data, heart rate data, eye movement data, or EEG output data, among other data) usable to determine whether the treatment is having an effect. In further examples, the usage data 252 is used to modify one or more aspects of the treatment automatically (e.g., a component of the bone conduction system 10 automatically modifies treatment parameters based on the usage data 252) or manually (e.g., the recipient or a healthcare provider makes the change manually). The monitoring of the usage can include monitoring events that occur while the bone conduction apparatus 100 is worn by the recipient, such as movement of a head of the recipient, which is described in more detail in FIG. 5. The monitoring of the usage can include monitoring an environment around the bone conduction apparatus 100, which is described in FIG. 6.

Customizing for Recipient

FIG. 3 illustrates a method 300 for customizing the bone conduction apparatus 100 for the recipient, such as in operation 222. The method 300 includes storing and loading parameters for the bone conduction apparatus. In examples, the bone conduction apparatus 100 is shared among multiple individuals or it is otherwise desirable to store parameters or other data in association with a profile that is able to be stored for later use. The method 300 includes operation 310.

Operation 310 includes producing calibration data 312 for the recipient. The calibration data 312 is data that calibrates or otherwise customizes the bone conduction apparatus 100 for the recipient. The calibration data 312 can include, for example, parameters that affect the generation of a therapeutic signal 232 by the therapeutic signal generator 112, such as by affecting an intensity, a frequency profile, a type, and a source of the therapeutic signal, among other parameters. The calibration data 312 can further include parameters that compensate for an amount of attenuation caused by the recipient's anatomy. The parameters can be stored in a data structure to form the calibration data 312. The calibration data 312 can be produced in any of a variety of ways. In examples, the calibration data 312 is set by the manufacturer of the bone conduction apparatus, a healthcare professional, the recipient, an algorithm (e.g., a machine learning algorithm trained to produce parameters based on input data regarding the recipient), or combinations thereof. Producing calibration data 312 can include one or more customizing procedures described above in relation to operation 222. In examples, the calibration data 312 is applied to the bone conduction apparatus 100 using a programmer device (e.g., the recipient computing device 20 or a special-purpose device for calibrating the bone conduction apparatus 100 to the recipient). Following operation 310, the flow of the method 300 moves to operation 320.

Operation 320 includes storing the calibration data 312 in association with a profile identifier 322. The profile identifier 322 is data usable to identify the recipient. The calibration data 312 is stored in association with the profile identifier 322 such that the profile identifier 322 can be used to obtain the calibration data 312. For instance, the profile identifier 322 can be used by a program to look up the calibration data 312 in a data structure and provide the profile identifier 322 as output. In some examples, the calibration data 312 is stored in the memory 140 of the bone conduction apparatus 100. In some examples, the calibration data 312 is stored at the recipient computing device 20 (e.g., stored in association with the application). In other examples, the calibration data 312 is stored at a server remote from the bone conduction apparatus 100 and the recipient computing device 20. Following operation 320, the flow of the method 300 moves to operation 330.

Operation 330 includes receiving the profile identifier 322. In examples, the profile identifier 322 is received at the bone conduction apparatus 100 (e.g., via the interface 132 thereof), at the recipient computing device 20 (e.g., via a touch screen thereof), at a server (e.g., via an application programming interface thereof), or another location. Following operation 330, the flow moves to operation 340.

Operation 340 includes selecting calibration data 312 using the profile identifier 322. In examples, selecting the calibration data 312 includes obtaining the calibration data 312 from memory or from a data structure using the profile identifier 322. Following operation 340, the flow moves to operation 350.

Operation 350 includes using the calibration data 312 to generate the therapeutic signal. The operation 350 can include providing the calibration data 312 to the bone conduction apparatus 100. For example, where the calibration data 312 is stored on the recipient computing device 20, the recipient computing device 20 (e.g., via an application thereof) sends the calibration data 312 to the bone conduction apparatus 100 for use in generating the therapeutic signal. Where the calibration data 312 is stored at a server, the server can send the calibration data 312 to the recipient computing device 20, which sends the calibration data 312 to the bone conduction apparatus 100 for use in generating the therapeutic signal. Where the calibration data 312 is stored at or sent to the bone conduction apparatus 100, the bone conduction apparatus 100 can use the calibration data 312 to set parameters for use in generating the therapeutic signal. Then the next time the therapeutic signal generator 112 produces the therapeutic signal, the therapeutic signal generator 112 uses the parameters set based on the calibration data 312 to produce the therapeutic signal 232 based on the parameters associated with the profile identifier 322. In this manner, the bone conduction apparatus 100 is customized to the recipient.

Generating Therapeutic Signals

Figure 4:
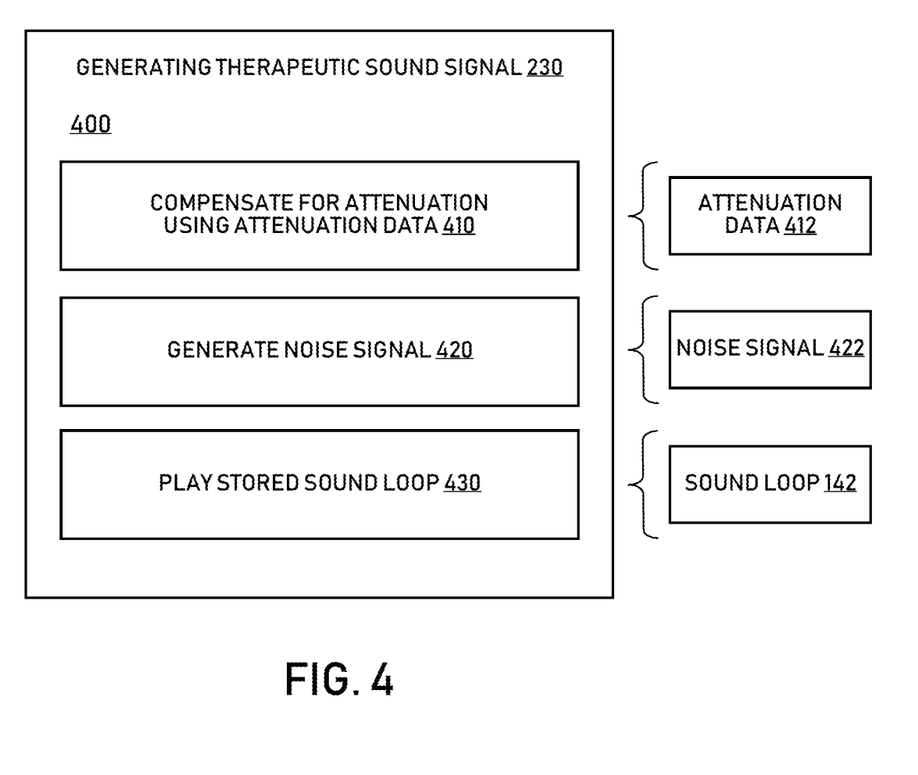
FIG. 4 illustrates a process for collecting recipient data.

FIG. 4 illustrates examples of generating the therapeutic signal 232 as described in operation 230. In some examples, generating the therapeutic signal 232 includes one or more of the following operations: operation 410, operation 420, and operation 430.

Operation 410 includes compensating for attenuation using attenuation data 412. In examples, compensating for attenuation includes modifying the therapeutic signal 232 such that a desired therapeutic sound percept is perceived by the recipient. For instance, attenuation of vibrations from the vibratory actuator 118 by tissue of the recipient can cause a desired therapeutic white noise to be perceived as pink noise. Compensating for the attenuation can include modifying the therapeutic signal 232 such that when the recipient perceives the vibrations, they are perceived as the desired white noise. The attenuation data 412 can include parameters (e.g., those described previously) that are usable to affect the therapeutic signal 232 to achieve desired characteristics. Modifying the therapeutic signal 232 can include modifying how the therapeutic signal 232 is generated (e.g., by modifying the parameters used to generate the therapeutic signal) such that when the therapeutic signal 232 is produced, it has desired characteristics. In other examples, the therapeutic signal 232 is modified after it has been produced (e.g., by applying filters to the therapeutic signal 232) to cause the therapeutic signal 232 to have desired characteristics.

Operation 420 includes generating a noise signal 422. For instance, the noise generator 114 is activated to produce a noise signal as output. In examples, the noise generator 114 generates the noise signal 422 using a digital or analog source of the noise. In some examples, the noise generator 114 includes a source of pseudo-randomness, the output of which is filtered to obtain desired noise characteristics (e.g., characteristics of white, brown, or pink noise).

Operation 430 includes playing a stored sound loop 142. For instance, the loop player 116 can load and play a sound loop 142 to produce the therapeutic signal 232 as output. In an example, the bone conduction apparatus 100 stores loops of therapeutic content (e.g., the sound loops 142 stored in the memory 140). The loop player 116 loads a stored sound loop 142 of therapeutic content and plays the sound loop 142 on repeat to produce the therapeutic signal 232 used by the vibratory actuator 118 to produce vibrations. In such examples, the output of the loop player 116 is the therapeutic signal 232 that is provided to the vibratory actuator 118.

Modifying Based on Head Movement

Figure 5:
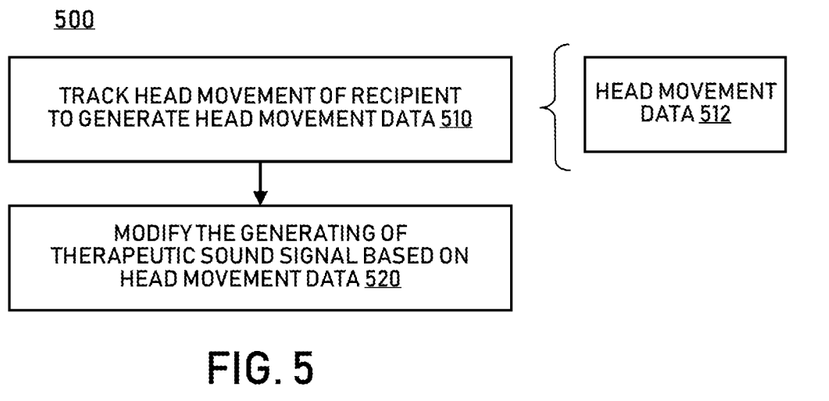
FIG. 5 illustrates a method for modifying the generating of the therapeutic signal based on head movement data.

FIG. 5 illustrates a method 500 for modifying the generating of the therapeutic signal 232 (e.g., as in operation 230) based on head movement data. As a specific example, a high level of head movement can indicate that the recipient is distracted and that the current level of treatment is not as effective as intended and should be modified.

The method 500 includes operation 510, which includes tracking head movement of the recipient to generate head movement data 512. Tracking head movement to generate the head movement data 512 can include obtaining data from one or more of the sensors 150. In many examples, tracking head movement data includes obtaining data from the gyroscopic sensor 152 and the accelerometer 154. Head movement data 512 can include an intensity and number of head movement events during a period of time. A head movement event is an instance of head movement. Following operation 510, the flow moves to operation 520.

Operation 520 includes modifying the generating of the therapeutic signal 232 based on the head movement data 512. In examples, head movement (e.g., an amount and an intensity thereof) can be used to infer the presence of an undesirable condition with the recipient. For instance, where the bone conduction apparatus 100 is provided for ameliorating a mental disorder of the recipient, an amount of head movement by the recipient can be used to infer the extent to which the mental disorder has a negative effect on the recipient and that treatment with the therapeutic signal 232 should be modified. An increase, decrease, or a lack of change in an amount of head movement can indicate that that the generation of the therapeutic signal 232 should be modified. Modifying the therapeutic signal 232 can include modifying the type, intensity, or other parameters of the generation of the therapeutic signal 232. Responsive to an amount of head movement being above a threshold amount of head movement for an amount of time above a time threshold, the bone conduction apparatus 100 can modify the generation of the therapeutic signal.

In addition to being used to modify the generation of the therapeutic signal, the head movement data 512 can be used to determine whether the treatment is having an intended effect on the recipient.

Modifying Based on Ambient Noise Level

Figure 6:
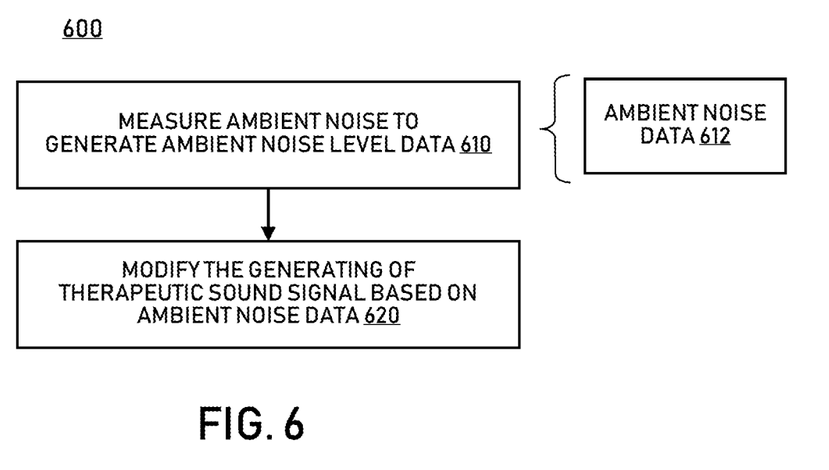
FIG. 6 illustrates a method for modifying the generating of the therapeutic signal based on an ambient noise level.

FIG. 6 illustrates a method 600 for modifying the generating of the therapeutic signal 232 (e.g., as in operation 230) based on ambient noise. For example, if the recipient is in an environment where a desirable ambient noise is present, the generation of the therapeutic signal 232 can be suspended until the desirable amount of ambient noise is no longer present.

The method includes operation 610, which includes measuring ambient noise to generate ambient noise data 612. The ambient noise data 612 is data regarding the sonic environment around the bone conduction apparatus 100. The ambient noise data 612 can include a volume of the ambient noise and a type of ambient noise, as well as other characteristics of the ambient noise. The bone conduction apparatus 100 can monitor the ambient noise to generate ambient noise data 612. For instance, the processor 130 can monitor an output of the microphone 156, and determine qualities of the ambient noise based thereon. In other examples, the recipient can specify the ambient noise data. For instance, the recipient computing device 20 can receive user input indicative of a volume of the sonic environment (e.g., based on selection of a button representative of a quiet, moderate, or loud sonic environment, among others) as well as user input indicative of a type of the sonic environment (e.g., based on selection of a button representative of lecture, conversation, or music, among others). Following operation 610, the flow moves to operation 620.

Operation 620 includes modifying the generating of the therapeutic signal 232 based on the ambient noise data 612. In some examples, this operation 620 includes modifying an intensity of the therapeutic signal 232 (e.g., thereby affecting the perceived volume of an auditory percept perceived based thereon) or a type of the therapeutic signal 232. In an example, the generation of the therapeutic signal 232 is set so that the perceived volume of the therapeutic sound percept is at least a threshold volume amount above an ambient noise volume. In other examples, the generation of the therapeutic signal 232 is set so that the recipient perceives sound percepts (e.g., whether from ambient sources or from bone conduction apparatus 100) at a minimum volume. For instance, while the ambient sources of sound are at or above a threshold level (e.g., 70 decibels, which is the noise of level of a typical coffee shop), the generation of the therapeutic signal 232 is reduced or stopped entirely, and while the ambient sources of sound are below the threshold level, the generation of the therapeutic signal 232 is set so that the user has a hearing percept from then bone conduction apparatus 100 equivalent to about 70 decibels.

In examples, modifying the generating of the therapeutic signal 232 is based on both the head movement data 512 and the ambient noise data 612. For example, high head movement can be undesirable in a quiet classroom, but may be appropriate in a noisy lunchroom. For instance, low levels of ambient noise may indicate that the recipient is in an environment in which high levels of activity (e.g., as measured by head movement) is undesirable. So responsive to the ambient noise data 612 indicating a quiet environment (e.g., below a threshold level of decibels) and the head movement data 512 indicating a high level of head movement (e.g., head movement above a threshold level), the generation of the therapeutic signal 232 can modified (e.g., increased in intensity).

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and methods to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

The invention claimed is:

1. A method, comprising:
   selecting a patient having a mental disorder and being treated for the mental disorder with a treatment plan including use of a pharmaceutical;
   providing a bone conduction apparatus to the patient;
   generating a therapeutic signal for ameliorating the mental disorder; and
   vibrating, using the therapeutic signal, a vibratory actuator of the bone conduction apparatus to cause the patient to perceive a therapeutic sound percept that supplements the treatment plan.

2. The method of claim 1, further comprising:
   tracking a head movement of the patient to generate head movement data; and
   modifying the generating of the therapeutic signal based on the head movement data.

3. The method of claim 1, wherein generating the therapeutic signal includes compensating the therapeutic signal for soft tissue attenuation.

4. The method of claim 3, wherein modifying the generating of the therapeutic signal includes:
   modifying an intensity level of the therapeutic signal; or
   modifying a type of therapeutic signal.

5. The method of claim 1, further comprising:
   measuring an ambient noise level to generate ambient noise level data; and
   modifying the generating of the therapeutic signal based on the ambient noise level data.

6. The method of claim 1, further comprising:
   monitoring usage of the bone conduction apparatus to generate usage data.

7. The method of claim 1, wherein generating the therapeutic signal includes:
   generating white noise, pink noise, or brown noise.

8. The method of claim 1, wherein generating the therapeutic signal includes:
   playing a stored therapeutic sound loop.

9. The method of claim 1, further comprising:
   wirelessly receiving the therapeutic signal at the bone conduction apparatus.

10. A bone conduction apparatus, comprising:
    a housing;
    a therapeutic sound system configured to solely generate therapeutic sound configured to address a mental disorder, the therapeutic sound system comprising:
      a sensor configured to track a head movement of a recipient of the bone conduction apparatus to generate head movement data, the recipient having the mental disorder;
      a signal generator configured to generate a therapeutic signal for ameliorating the mental disorder and modify generation of the therapeutic signal based on the head movement data;
      a vibratory actuator disposed in the housing and configured to vibrate in response to the therapeutic signal; and
      a coupling apparatus to facilitate transfer of vibrations from the vibratory actuator to a cochlea of the recipient of the bone conduction apparatus via the skull of the recipient to cause the recipient to perceive a therapeutic sound percept.

11. The bone conduction apparatus of claim 10, further comprising:
    a memory having stored thereon one or more therapeutic sound loops,
    wherein the signal generator is configured to generate the therapeutic signal from the one or more therapeutic sound loops.

12. The bone conduction apparatus of claim 10, wherein the sensor comprises a gyroscopic sensor or an accelerometer.

13. The bone conduction apparatus of claim 10, wherein the signal generator is remote from the housing.

14. The bone conduction apparatus of claim 10, wherein the signal generator is configured to, when generating the therapeutic signal, compensate for soft tissue attenuation during transmission of vibrations to the cochlea of the recipient of the bone conduction apparatus.

15. A method comprising:
    providing a bone conduction apparatus to a recipient prior to the recipient performing a task;
    calibrating the bone conduction apparatus to the recipient to generate calibration data; and
    while the recipient is performing the task and wearing the bone conduction apparatus:
      generating a predetermined therapeutic signal based on the calibration data; and
      vibrating, based on the predetermined therapeutic signal, a vibratory actuator of the bone conduction apparatus to cause the recipient to receive a therapeutic sound percept.

16. The method of claim 15, further comprising:
    monitoring a usage of the bone conduction apparatus to generate usage data;
    tracking head movement of the recipient to generate head movement data; and
    providing the usage data and the head movement data as output.

17. The method of claim 15, further comprising:
    receiving a profile identifier; and
    selecting the calibration data from a calibration data set using the profile identifier.

18. The method of claim 15, wherein generating the predetermined therapeutic signal includes:
    generating a white noise signal;
    generating a pink noise signal; or
    generating a brown noise signal.

* * * * *